(12) United States Patent
Mercati

(10) Patent No.: US 6,838,092 B2
(45) Date of Patent: Jan. 4, 2005

(54) EFFERVESCENT COMPOSITIONS CONTAINING DRIED FRUIT JUICES

(75) Inventor: Valentino Mercati, Sansepolcro (IT)

(73) Assignee: Aboca S.p.A., Sansepolcro (IT)

(*) Notice: Subject to any disclaimer, the term of this patent is extended or adjusted under 35 U.S.C. 154(b) by 0 days.

(21) Appl. No.: 10/401,673

(22) Filed: Mar. 31, 2003

(65) Prior Publication Data

US 2003/0194435 A1 Oct. 16, 2003

(30) Foreign Application Priority Data

Apr. 9, 2002 (IT) ..................... MI2002A0754

(51) Int. Cl.⁷ ................................................. A61K 9/46
(52) U.S. Cl. ..................................................... 424/466
(58) Field of Search ................................ 424/466, 400, 424/464, 465; 426/567; 167/57

(56) References Cited

U.S. PATENT DOCUMENTS 2,147,743 A * 2/1939 Levin et al.
5,401,513 A * 3/1995 Wehling et al.
2003/0068422 A1 * 4/2003 Rivier ........................ 426/567

FOREIGN PATENT DOCUMENTS

| EP | 0 919 227 A1 | 6/1999 |
| EP | 0 911 032 B1 | 3/2002 |
| EP | 0 922 450 B1 | 4/2003 |

* cited by examiner

Primary Examiner—James M. Spear
Assistant Examiner—Retford Berko
(74) Attorney, Agent, or Firm—Young & Thompson

(57) ABSTRACT

The present invention relates to effervescent compositions containing active ingredients, in particular dry plant extracts, wherein the acid donor of the effervescent couple is constituted by a dried fruit juice with a natural acid pH, such as freeze-dried citrus fruit juice.

12 Claims, No Drawings

EFFERVESCENT COMPOSITIONS CONTAINING DRIED FRUIT JUICES

FIELD OF THE INVENTION

The present invention relates to effervescent compositions containing dried fruit juices.

More particularly, the present invention relates to effervescent compositions containing dried fruit juices, a source of carbon dioxide and an acid donor, wherein the acid donor is constituted by a dried fruit juice with a natural acid pH.

The invention also relates to the process for the preparation of said effervescent compositions.

TECHNICAL BACKGROUND

The growing success in recent years of phytotherapy preparations based on plant extracts has led to research into formulations with a safer, more reproducible unit dosage than the traditional preparations made by infusion.

Of the various formulations proposed, effervescent preparations based on dry plant extracts have encountered the favour of the public because they dissolve easily, generally have a pleasant flavour and are easier to use than solid forms, which are sometimes relatively large and therefore difficult to swallow. However, this type of preparation also presents some drawbacks.

In effervescent preparations in the form of tablets or granulate, the effervescence is caused by the carbon dioxide generated by the reaction between an acid (usually citric or tartaric acid) and sodium or potassium bicarbonate. The effervescence sometimes develops in a very violent way, causing excessively rapid hydration of the dry plant extracts contained in the tablet or granule, and leading to the formation of a layer of highly concentrated solution which prevents the water from reaching the innermost part of the tablet or granule, thus delaying and sometimes even preventing complete dissolution of the preparation.

Another problem closely connected with effervescence, and consequently with excessively violent hydration, is the formation of a thick layer of froth, which once again slows complete dissolution of the preparation. Plant extracts, which are often rich in saponin, are particularly liable to froth formation.

Another problem with effervescent formulations is their instability in the presence of moisture.

In an attempt to solve these problems, coating the particles of plant extract with oily, waxy or fatty substances (EP-A-911032) or using a surplus of water-soluble medium (EP-A-922450, EP-A-919227) has been proposed. However, these solutions are not wholly satisfactory because they involve formulation difficulties associated with coating techniques and the use of large amounts of excipients.

DISCLOSURE OF THE INVENTION

The problems with the prior art are overcome by the effervescent compositions of the present invention, which are characterised by an acid donor constituted by a dried fruit juice with a natural acid pH.

According to the invention, the term "dried fruit juice with a natural acid pH" means a product obtainable by drying, for example by evaporation, spray-drying or freeze-drying (possibly in the presence of suitable media) an edible plant juice with a water content ranging from 30 to 70%, which has a pH of less than 5, and preferably less than 4, as a result of a content in organic acids such as citric acid, tartaric acid, malic acid, etc. Fruit juices such as citrus fruit juices (lemon, orange and grapefruit), red fruit juices (bilberry, blackberry, aronia, soft fruits, cherry, strawberry, sour cherry, cranberry and plum), apple, pineapple and tamarind, either alone or in association thereof can preferably be used.

According to a preferred aspect of the present invention, the fruit juice is citrus fruit juice.

According to another preferred aspect of the invention, the dried juice is obtained by freeze-drying in the presence of a medium in the dry or powdered state which can be dispersed, suspended or solubilised in water. Examples of suitable media are sugars and polyalcohols such as lactose, fructose and mannitol, or complex carbohydrates such as inulin, starches, microcrystalline cellulose, or other inert excipients such as magnesium stearate or talc.

The dry extracts which preferably constitute the active ingredients of the compositions of the invention may be extracts of natural (plant or animal) origin which are conventionally used in traditional medicine or phytotherapy, with a protective activity or one which promotes the physiological well-being of the body, obtainable by equally conventional methods, such as by extraction of the part of the plant containing the active ingredient with a suitable solvent and its subsequent elimination by evaporation or freeze-drying.

Examples of extracts which can be advantageously formulated according to the invention include royal jelly, propolis, extracts of Echinacea, acerola, artichoke, milkthistle, ginseng, Eleutherococcus, passion flower, camomile, rhubarb, astragalus, spiraea, willow, calendula, goldenrod, black cohosh, gentian, cinchona, liquorice, devil's claw, hare's-ear, centella, gingko, incense, karkade, lemon balm, mint, olive, Californian poppy, valerian, butcher's broom, dandelion, green tea, squawberry, red vine, withania, etc.

Alkali carbonates or bicarbonates such as sodium or potassium bicarbonate can be used as carbon dioxide source.

The quantitative ratios of the dried juice to the carbon dioxide source will depend on the acid content of the juice, and can be determined by those skilled in the art by conventional methods so as to guarantee an almost quantitative reaction between the acid and basic constituents of the effervescent couple with optimum times and degrees of effervescence.

Broadly speaking, 1 to 3 kg of juice will be used for every kilo of dried plant juice, and more commonly approx. 1.5 to 2 kg of juice and 0.05 to 0.4 kg of sodium or potassium bicarbonate or carbonate. If a freeze-dried juice is used in a medium, the medium will constitute 30 to 60% by weight on the total, as the percentage by weight of dehydrated juice is between 40 and 70%.

The process for the preparation of dried juice in a medium comprises the following steps:

1. The powdered medium is solubilised, dispersed or suspended in water;
2. The acid-containing fruit juice is homogeneously mixed with the aqueous phase containing the medium;
3. As an alternative to steps a and b, the medium can be solubilised, dispersed or suspended directly in the juice, after dilution in water if required;
4. The mixture is dried;
5. The resulting dry extract is pulverised.

More particularly, the medium is dispersed under stirring, in an amount ranging between 0.2 and 0.6 kg, in the pre-set amount of water, which can range between 3 and 6 kg. This dissolution is performed at a suitable temperature in a time of 10 to 60 minutes. When the medium is fully dispersed, the fruit juice is added under stirring to this solution, either alone or associated with other juices in a weight ranging between 1 and 3 kg, so as to produce a homogenous mixture.

This mixture can be dried with, for example, a freeze-drying process according to the following cycle:

- introduction of the mixture into a tray in a 2–8 cm layer;
- freezing of the mixture to the temperature of −30/−50° C.;
- formation of a vacuum with a value ranging between 90 and 180 microbars in the freeze-drying chamber;
- heat inversion of the temperature with heating at 30–40° C. for a time of 48 to 96 hours, until complete dehydration of the product.

The dried product obtained at the end of the cycle is ground to a fine powder.

This dry extract is then mixed homogeneously with the carbon dioxide source, such as sodium bicarbonate, and with the active ingredients of plant or animal origin, to obtain the final effervescent formulation.

The compositions according to the invention may be in the form of effervescent tablets or granulates/powders in sachets, obtainable by conventional granulation and/or compression methods. Sweeteners such as saccharose, freeze-dried honey, fructose, aspartame, saccharine, flavourings, food dyes and other excipients conventionally used may be added if required.

The use of a fruit juice dried by freeze-drying on a medium such as inulin offers the following main advantages:

1) The effervescence generated is less violent because there is less acid-base contact due to the presence of the medium; infact, carbon dioxide is in fact generated more slowly because the acid in the juice must first "separate" from the medium in which it is incorporated, and then react gradually with the base.
2) The result is that dry extracts, added to the formulation for their functional activity, have time to hydrate better and dissolve in the time for which the effervescence lasts, and thus generate less foam.
3) The final formulation is more stable because the acid is incorporated in the medium and has less contact with the base, which involves fewer problems of reactions in the presence of moisture.

It is not necessary to add excipients which act as fillers to the mixture, as the same function is already performed by the freeze-drying medium; each raw material, other than the extract containing the acid, the basic carbonate and the functional plant extracts, is included solely to improve the pleasantness of the drink.

Dried juices with a natural acid pH can also be used as acid donors in effervescent formulations of active ingredients which need not necessarily be plant extracts.

Examples of formulations according to the invention are set out below.

Example 1
Formulation A (Granulate in Sachets)

| FORMULATION A | % |
|---|---|
| Dried orange juice on inulin | 42.44 |
| Dried lemon juice on inulin | 20.79 |
| Sweetener (e.g. fructose/sugar/dried honey, synthetic sweeteners) | 25.77 |
| Sodium bicarbonate | 5.55 |
| Echinacea dry extract | 2.78 |
| Acerola dry extract | 2 |
| Propolis dry extract | 0.67 |
| Duration of effervescence | 2 minutes |
| pH of final solution | 4.21 |

Example 2
Formulation B (Granulate in Sachets)

| FORMULATION B | % |
|---|---|
| Sweetener (e.g. fructose/sugar/dried honey, synthetic sweeteners) | 71.7 |
| Dried lemon juice on inulin | 18.8 |
| Sodium bicarbonate | 4 |
| Milk-thistle dry extract | 1 |
| Artichoke dry extract | 1 |
| Liquorice dry extract | 1 |
| Cinchona dry extract | 0.5 |
| Gentian dry extract | 0.5 |
| Rhubarb dry extract | 0.5 |
| Boldo dry extract | 0.5 |
| Duration of effervescence | 2.5 minutes |
| pH of final solution | 4.35 |

Example 3
Formulation C (Granulate in Sachets)

| FORMULATION C | % |
|---|---|
| Sweetener (e.g. fructose/sugar/dried honey, synthetic sweeteners) | 38.93 |
| Dried lemon juice on inulin | 30 |
| Sodium bicarbonate | 5.4 |
| Spiraea dry extract | 6.67 |
| Acerola dry extract | 6 |
| Astragalus dry extract | 5 |
| Echinacea dry extract | 4 |
| Zinc gluconate | 3.5 |
| Flavouring | 0.4 |
| Dye | 0.1 |
| Duration of effervescence | 2.5 minutes |
| pH of final solution | 4.14 |

Example 4
Formulation D (Granulate in Sachets)

| FORMULATION D | % |
|---|---|
| Sweetener (e.g. fructose/sugar/dried honey, synthetic sweeteners) | 26.1 |
| Dried lemon juice on inulin | 18.8 |
| Dried bilberry juice on inulin | 46.3 |
| Sodium bicarbonate | 5.6 |
| Ginseng dry extract | 1.6 |
| Withania dry extract | 1.1 |
| Eleutherococcus dry extract | 0.5 |
| Duration of effervescence | 2 minutes |
| pH of final solution | 4.25 |

Example 5
Formulation E (Effervescent Tablets)

| FORMULATION E | % |
|---|---|
| Fructose | 39 |
| Dried honey | 10 |
| Dried lemon juice on inulin | 28.5 |
| Sodium bicarbonate | 5.9 |
| Propolis dry extract | 2.5 |

-continued

| FORMULATION E | % |
| --- | --- |
| Acerola dry extract | 2.1 |
| Yeast with zinc | 7 |
| Carrot dry extract | 5 |
| Duration of effervescence | 4 minutes |
| pH of final solution | 4.55 |

What is claimed is:

1. Effervescent compositions containing one or more active ingredients, a source of carbon dioxide and an acid donor, characterised in that the acid donor is constituted by a dried fruit juice with a natural acid pH.

2. Effervescent compositions as claimed in claim 1, wherein the active ingredients are dry plant extracts.

3. Effervescent compositions as claimed in claim 1, wherein the fruit juice is a juice containing organic acids, selected from the group consisting of citrus fruit, red fruit, apple, pineapple and tamarind juices, either alone or in association thereof.

4. Effervescent compositions as claimed in claim 3, wherein the fruit juice is citrus fruit juice.

5. Effervescent compositions as claimed in claim 1, wherein the fruit juice is dried by freeze-drying in the presence of a medium selected from sugars, complex carbohydrates, magnesium stearate and talc.

6. Effervescent compositions as claimed in claim 5, wherein the medium is a simple or complex sugar selected from lactose, fructose, mannitol, inulin, starches and microcrystalline cellulose.

7. Effervescent compositions as claimed in claim 6, wherein the medium is inulin.

8. Effervescent compositions as claimed in claim 1, wherein the source of carbon dioxide is an alkali carbonate or bicarbonate.

9. Effervescent compositions as claimed in claim 1, containing one or more active ingredients selected from royal jelly, propolis; Echinacea, acerola, artichoke, milk-thistle, ginseng, Eleutherococcus, passion flower, camomile, rhubarb, astragalus, spiraea, willow, calendula, goldenrod, black cohosh, gentian, cinchona, liquorice, devil's claw, hare's-ear, centella, gingko, incense, karkadé, lemon balm, mint, olive, Californian poppy, valerian, butcher's broom, dandelion, green tea, squawberry, red vine and withania extracts.

10. Effervescent compositions according to claim 1 in the form of tablets or sachets of granulate.

11. A process for the preparation of the effervescent compositions as claimed in claim 1, comprising the following steps:

a) solubilisation, dispersion or suspension of a powdered medium selected from sugars, carbohydrates, talc or magnesium stearate in water;

b) homogenous mixing of fruit juice with the aqueous phase containing the medium;

c) as an alternative to steps a) and b), solubilisation, dispersion or suspension of the medium directly in the juice, after dilution in water if required;

d) drying of the mixture;

e) pulverisation of the resulting dry extract;

f) mixing of the dry extract prepared in d) with an alkali carbonate or bicarbonate;

g) addition of one or more active ingredients to the effervescent mixture prepared in e).

12. A process as claimed in claim 11, wherein the weight ratio between the medium, water and fruit juice falls into the range 0.2–0.6:3–6:1–3.

* * * * *